United States Patent
Wagner et al.

[11] Patent Number: 5,936,093
[45] Date of Patent: Aug. 10, 1999

[54] PROCESS FOR PREPARING PYRIDYLMETHYL ISOTHIOCYANATES

[75] Inventors: Klaus Wagner, Köln; Reinhard Lantzsch, Wuppertal, both of Germany

[73] Assignee: Bayer Aktiengesellschaft, Leverkusen, Germany

[21] Appl. No.: 09/116,267

[22] Filed: Jul. 16, 1998

[30] Foreign Application Priority Data

Jul. 24, 1997 [DE] Germany .......................... 197 31 782

[51] Int. Cl.$^6$ ............................................... C07D 213/38
[52] U.S. Cl. ................................................................ 546/331
[58] Field of Search .............................................. 546/331

[56] References Cited

U.S. PATENT DOCUMENTS 4,129,656 12/1978 Lang et al. ............................. 424/263
5,175,301 12/1992 Mimamida et al. .................... 546/272

FOREIGN PATENT DOCUMENTS 302389  2/1989  European Pat. Off. .

OTHER PUBLICATIONS

Database XFIRE Beilstein, Raction ID2437787 and 2626662, 1980, Rahman M.F. "Synthesis of 4-substituted thiosemicarbazones of . . . agents" XP002077168.

*Primary Examiner*—Patricia L. Morris
*Attorney, Agent, or Firm*—Sprung Kramer Schaefer & Briscoe

[57] ABSTRACT

Process for preparing pyridylmethyl isothiocyanates of the formula (I)

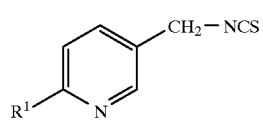

(I)

comprising reacting amines of the formula (II):

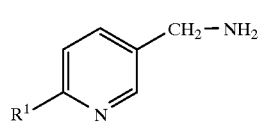

(II)

with xanthogenates of the formula (III):

$$R^2O\text{—}CS\text{—}S^\ominus M^\oplus \qquad (III)$$

and oxidizing the resulting dithiocarbamates of the formula (IV):

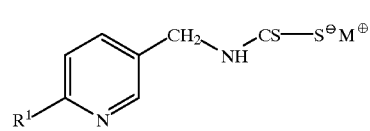

(IV)

wherein $R^1$ represents halogen or alkyl; $R^2$ represents alkyl; and M represents an alkali metal or ammonium.

5 Claims, No Drawings

PROCESS FOR PREPARING PYRIDYLMETHYL ISOTHIOCYANATES

The present invention relates to a novel process for preparing pyridylmethyl isothiocyanates and to novel intermediates.

It is known that pyridylmethyl isothiocyanates are obtained when pyridylmethyl amines of the formula (A) are reacted with carbon disulfide and, for example, ethyl chloroformate in the presence of a base, such as, for example, sodium hydroxide, according to the following equation:

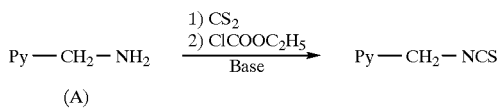

(A)

Py=optionally substituted pyridyl, such as, for example, 2-chloro-5-pyridyl (cf. EP-A 0 302 389).

However, this process has the disadvantage that carbon disulfide is employed as reaction partner. Furthermore, carbon oxysulfide is obtained as byproduct.

It has now been found that pyridylmethyl isothiocyanates of the formula (I)

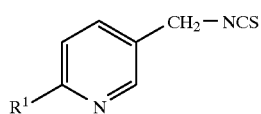
(I)

in which $R^1$ represents halogen or $C_1$–$C_4$-alkyl are obtained in good yields and high purity when in a first step, amines of the formula (II)

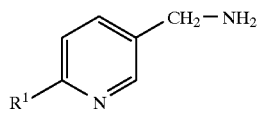
(II)

in which $R^1$ is as defined above, are reacted with xanthogenates of the formula (III)

$R^2O$—CS—$S^\ominus M^\oplus$ (III)

in which $R^2$ represents $C_1$–$C_4$-alkyl, preferably methyl or ethyl and

M represents an alkali metal, preferably sodium and potassium or represents ammonium, if appropriate in the presence of a diluent, and in a second step, the resulting dithiocarbamates of the formula (IV)

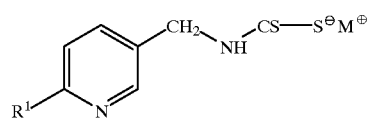
(IV)

in which $R^1$ and M are each as defined above, are oxidized, if appropriate in the presence of a diluent, to give the isothiocyanates of the formula (I).

The formula (I) provides a general definition of the pyridylmethyl isothiocyanates preparable according to the invention. In this formula, $R^1$ preferably represents chlorine or methyl.

Surprisingly, the pyridylmethyl isothiocyanates of the formula (I) can be obtained in good yields and in high purity by the process according to the invention, although the sulfur-containing radical MSH in the xanthogenates of the formula (III) is the better leaving group as compared to the alcohol radical $R^2OH$ and the following course of reaction could therefore have been expected:

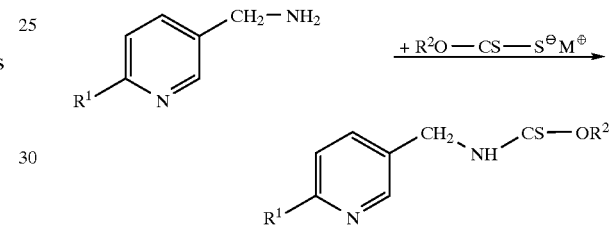

The reaction according to the invention has the advantage that carbon disulfide is not required as reaction partner. Moreover, the practice of the reaction is simple (no exothermic reaction) and the reaction proceeds without side reactions.

Using, for example, 5-aminomethyl-2-chloropyridine and potassium ethyl xanthogenate as starting materials and aqueous NaOCl solution as oxidizing agent, the course of the reaction of the process according to the invention can be illustrated by the following equation:

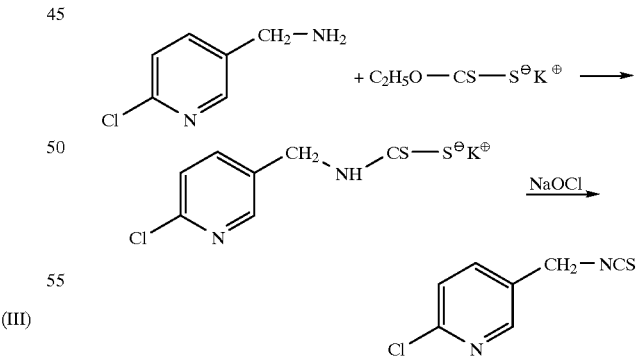

The amines of the formula (II) to be used as starting materials in the first step of the process according to the invention are known (cf., for example, EP-A 0 391 205 or US-P 4 499 097) and/or can be obtained in a generally known manner.

The xanthogenates of the formula (III) furthermore to be used as starting materials in the first step of the process according to the invention are generally known compounds.

The formula (IV) provides a general definition of the dithiocarbamates obtainable in the first step of the process according to the invention. In this formula, $R^1$ preferably represents chlorine or methyl and M preferably represents sodium, potassium or ammonium.

The dithiocarbamates of the formula (IV) are novel and also form part of the subject matter of the present application.

Preferred oxidizing agents for the second step of the process according to the invention are: sodium hypochlorite or potassium hypochlorite solution and copper(II) compounds, such as copper sulfate.

Suitable diluents for the first step of the process according to the invention are customary organic solvents. These preferably include hydrocarbons, such as toluene or xylene; ethers such as methyl tert-butyl ether, methyl tert-amyl ether, 1,2-dimethoxyethane, 1,2-diethoxyethane, tetrahydrofuran or dioxane; alcohols, such as methanol, ethanol, n-propanol, i-propanol, n-, i-, s- or t-butanol; nitriles, such as acetonitrile, propionitrile or butyronitrile; and amides, such as dimethylformamide.

When carrying out the first step of the process according to the invention, the reaction temperatures can be varied within a relatively wide range. In general, the reaction is carried out at temperatures between 30° C. and 150° C., preferably at temperatures between 50° C. and 120° C.

When carrying out the first step of the process according to the invention, preference is given to employing equimolar amounts. However, it is also possible to employ a relatively large excess of the cheaper xanthogenate of the formula (III), preferably 100%.

The reaction is carried out and the novel dithiocarbamates of the formula (IV) are worked up and isolated in a generally customary manner (cf. also the Preparation Example).

Preferred diluents for the oxidation according to the second step of the process according to the invention are water and a second inert, sparingly water-miscible solvent, such as, for example, hydrocarbons, chlorinated hydrocarbons, ethers, nitriles, ketones or amides.

When carrying out the second step of the process according to the invention, the reaction temperatures can be varied within a relatively wide range. In general, the reaction is carried out at temperatures between −30° C. and 50° C., preferably at temperatures between −10° C. and 10° C.

When carrying out the second step of the process according to the invention, generally 4 to 5 mol, preferably 4 to 4.5 mol, of oxidizing agent are employed per mole of dithiocarbamate.

The reaction is carried out and the pyridylmethyl isothiocyanates of the formula (I) are worked up and isolated in a generally customary manner (cf. also the Preparation Example).

The pyridylmethyl isothiocyanates of the formula (I) to be prepared by the process according to the invention can be used as intermediates for preparing biologically active compounds, for example insecticides (cf., for example, EP-A 0 302 389).

PREPARATION EXAMPLES

Example 1

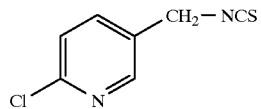

(Second Step)

51.3 g (0.2 mol) of potassium 2-chloro-5-pyridylmethyldithiocarbamate (cf. first step) are dissolved in 200 ml of water and admixed with 200 ml of methylene chloride.

At 0° C., 460 ml of 13% strength aqueous NaOCl solution are added dropwise in such a manner that the temperature does not exceed 5° C. The mixture is stirred at 0–5° C. for 30 minutes, the organic phase is separated off, the aqueous phase is extracted three times with methylene chloride and the combined organic phases are dried with sodium sulfate.

The solvent is distilled off, giving 31.3 g (82% of theory) of 2-chloro-5-pyridylmethyl isothiocyanate which crystallizes in the fridge (melting point: 22° C.)

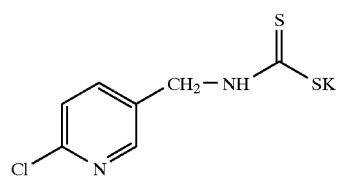

(II-1)

(First Step)

2.85 g (20 mmol) of 2-chloro-5-aminomethyl-pyridine and 3.2 g (20 mmol) of potassium ethylxanthogenate in 30 ml of ethanol are stirred under reflux overnight.

The mixture is allowed to cool and filtered off: This gives 4.4 g (86% of theory) of potassium 2-chloro-5-pyridylmethyldithiocarbamate of melting point 252° C. (decomp.).

We claim:

1. Process for preparing a pyridylmethyl isothiocyanate of the formula

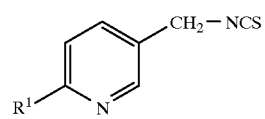

(I)

in which $R^1$ represents halogen or $C_1$–$C_4$-alkyl, said process comprising in a first step, reacting an amine of the formula

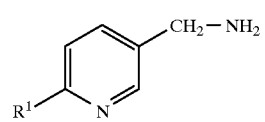

(II)

in which
R$^1$ is as defined above, $$R^2O-CS-S^\ominus M^\oplus \quad (III)$$

in which
R$^2$ represents C$_1$–C$_4$-alkyl and
M represents an alkali metal or represents ammonium,
at a temperature between 30° C. and 150° C. and in the presence of a diluent, to yield a dithiocarbomate of the formula (IV):

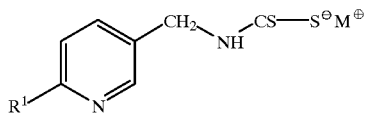

(IV)

in which
R$^1$ and M are each as defined above,
and, in a second step, oxidizing the dithiocarbamate of the formula (IV) at temperatures between −30° C. and 50° C., and in the presence of a diluent to yield the isothiocyanate of the formula (I).

2. A process according to claim 1 where the diluent used in the first step is selected from the group consisting of: aromatic or aliphatic hydrocarbons, ethers, alcohols, nitriles and amides, and the diluent used in the second step is a two-phase system consisting of water and an inert and only weakly water-miscible solvent.

3. Process according to claim 1 where the diluent used in the first step is selected from the group consisting of: toluene, ethanol and n-butanol, and the diluent used in the second step is a two-phase system consisting of water and an organic solvent selected from the group consisting of toluene, chlorobenzene, methylenechloride and n-butanol.

4. A process according to claim 1 where step one is carried out at a temperature between 50° C. and 120° C. and the second step is carried out at a temperature between −10° C. and 10° C.

5. A process according to claim 1 where the oxidizing agent used in the second step is selected from the group consisting of sodium hypochlorite, potassium hypochlorite and copper (II) compounds.

* * * * *